(12) United States Patent
Bell

(10) Patent No.: US 7,431,883 B2
(45) Date of Patent: Oct. 7, 2008

(54) CLINICAL ANALYSIS SYSTEM

(75) Inventor: Michael L. Bell, Fullerton, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 789 days.

(21) Appl. No.: 10/676,349

(22) Filed: Sep. 30, 2003

(65) Prior Publication Data

US 2005/0069454 A1    Mar. 31, 2005

(51) Int. Cl.
*G01N 21/00*    (2006.01)

(52) U.S. Cl. ............................. 422/67; 422/63; 422/64; 422/65; 422/66; 422/99; 422/100; 436/180

(58) Field of Classification Search ............. 422/63–65, 422/99–100; 436/180
See application file for complete search history.

(56) References Cited

U.S. PATENT DOCUMENTS

| | | | |
|---|---|---|---|
| 3,561,186 A | 2/1971 | Pickering | 53/22 |
| 3,579,303 A | 5/1971 | Pickering | 23/230 |
| 3,768,978 A | 10/1973 | Grubb et al. | 23/259 |
| 4,212,204 A | 7/1980 | St. Amand | 73/425.6 |
| 4,276,048 A | 6/1981 | Leaback | 23/230 |
| 4,288,228 A | 9/1981 | Oberhardt | 23/230 |
| 4,331,962 A | 5/1982 | Neumann | 346/33 ME |
| 4,680,270 A * | 7/1987 | Mitsumaki et al. | 205/778 |
| 4,737,910 A | 4/1988 | Kimbrow | 364/403 |
| 5,040,890 A | 8/1991 | North, Jr. | 356/72 |
| 5,130,095 A * | 7/1992 | Ricchio et al. | 422/63 |
| 5,304,487 A | 4/1994 | Wilding | 435/291 |
| 5,437,200 A | 8/1995 | Hollinger | 73/863.73 |
| 5,486,335 A | 1/1996 | Wilding et al. | 422/55 |
| 5,519,635 A | 5/1996 | Miyake et al. | 364/497 |
| 5,601,115 A | 2/1997 | Broerman | 137/595 |
| 5,614,415 A | 3/1997 | Markin | 436/48 |
| 5,631,844 A | 5/1997 | Margery et al. | 364/496 |
| 5,639,423 A | 6/1997 | Northrup et al. | 122/50 |
| 5,690,895 A | 11/1997 | Matsumoto et al. | 422/73 |
| 5,955,028 A | 9/1999 | Chow | 422/63 |

(Continued)

FOREIGN PATENT DOCUMENTS

EP    0 252 631    1/1988

(Continued)

*Primary Examiner*—Jill Warden
*Assistant Examiner*—Jyoti Nagpaul
(74) *Attorney, Agent, or Firm*—Townsend and Townsend and Crew, LLP; Anne M. Murphy (57) ABSTRACT

A system for analyzing samples having a portable analysis unit and a base unit. The portable analysis unit has a sample inlet, an analyzer, a reagent supply reservoir, a collection reservoir for waste, a reagent inlet for providing reagent to the supply reservoir, a waste outlet for removing waste from the collection reservoir, a supply conduit from the reagent supply reservoir to the analyzer, a waste conduit from the analyzer to the collection reservoir, a power source, a data output element, and a pressure source for moving reagent and waste. The base unit is connectable to the analyzer unit for providing reagent and receiving waste. The base unit has a reagent storage reservoir, a waste storage reservoir, a waste inlet for connection to the waste outlet; and an outlet for providing reagent from the reagent storage reservoir to the reagent inlet.

22 Claims, 7 Drawing Sheets

U.S. PATENT DOCUMENTS

| | | | |
|---|---|---|---|
| 6,165,739 A | 12/2000 | Clatch | 435/29 |
| 6,209,928 B1 | 4/2001 | Benett et al. | 285/124.1 |
| 6,249,774 B1 | 6/2001 | Roden et al. | 705/28 |
| 6,267,143 B1 | 7/2001 | Schick | 137/625.11 |
| 6,273,478 B1 | 8/2001 | Benett et al. | 285/346 |
| 6,524,240 B1 | 2/2003 | Thede | 600/300 |
| 2001/0043882 A1 | 11/2001 | Berger et al. | 422/67 |

FOREIGN PATENT DOCUMENTS

| | | |
|---|---|---|
| WO | WO 02/10713 | 2/2002 |

* cited by examiner

CLINICAL ANALYSIS SYSTEM

BACKGROUND

The present invention relates to clinical analysis kits and, more particularly, to a modular clinical analysis system having a base unit and an analysis unit.

The medical condition of a patient is often reflected by body chemistry. Accordingly, diagnostic medicine has developed a variety of analytical techniques to measure the presence and concentration of numerous test substances which serve as indicators of disease states or abnormalities. The great complexity of living organisms and the number and variety of substances for which detection and quantitative measurement may be helpful in identifying or excluding possible disease states or medical conditions has made it generally necessary to carry out a number of different tests. Additionally, many environmental systems may be chemically analyzed for the presence and concentration of desirable and undesirable elements.

Often analysis of patients and environmental systems is conducted in the field away from complex laboratory facilities. It is desirable to have a diagnostic device capable of being easily moved into the field for analysis. Portable diagnostic devices are known. However, these devices are often limited in their capability to transmit and retain test results. Often these devices are only usable one time before being discarded, which adds significant expense. Often these devices are incapable of processing as many different types of analytes as desired.

Alternatively, samples may be transported back to a central laboratory where the sample is processed and the results reported back to the test requester. This process is costly, time consuming, and can introduce contamination to the sample. Additionally, some samples are hard to transport.

Therefore, a need exists for an improved diagnostic device capable of being moved into the field for analysis.

SUMMARY

The present invention is directed to a system for analyzing samples. A system for analyzing samples according to one embodiment of the present invention comprises a portable analysis unit and a base unit.

The portable analysis unit comprises a sample inlet; an analyzer for determining a characteristic of a sample and providing data about the characteristic; a reagent supply reservoir; a collection reservoir for waste comprising used reagent and analyzed sample; a reagent inlet for providing reagent to the supply reservoir; a waste outlet for removing waste from the collection reservoir; a supply conduit from the reagent supply reservoir to the analyzer; a waste conduit from the analyzer to the collection reservoir; a power source for providing power to the analyzer; a data output element for outputting data generated by the analyzer; and a pressure source for moving reagent and waste.

The base unit is adapted for connection to the analyzer unit, for providing reagent to the analysis unit, and for receiving waste from the collection reservoir. The base unit comprises a reagent storage reservoir; a waste storage reservoir; a waste inlet for connection to the waste outlet of the analysis unit for receiving waste from the analysis unit; and a reagent outlet for providing reagent from the reagent storage reservoir to the reagent inlet of the analysis unit.

Optionally, the portable analysis unit further comprises a multiport valve coupled to the pressure source, the supply conduit and the waste conduit. The portable analysis unit can also have a reaction chamber disposed in fluid tight communication with the multiport valve.

Optionally, the analysis unit reagent supply reservoir further comprises a wash fluid supply reservoir; and a wash fluid inlet for providing wash fluid to the wash fluid supply reservoir; and the base unit reagent storage reservoir further comprises a wash fluid storage reservoir; and a wash fluid outlet for providing wash fluid to the wash fluid inlet of the analysis unit.

The analyzer can be a cytometer flow cell. The cytometer flow cell can have a core stream hydrodynamically focused by a sheath flow.

Optionally, the portable analysis unit further comprises a controller controlling the analyzer and the multiport valve. The controller comprises a microcomputer capable of inputting data and outputting data. The analysis unit may further comprise a user input device for inputting data into the analysis unit microcomputer. Optionally, the controller contains a set of instructions for at least one of directing the automatic self-cleaning of the analysis unit, directing the automatic self-calibrating of the analysis unit, directing the automatic self-replenishing of reagents in the reagent supply reservoir, directing the automatic self-testing of the analysis unit.

The present invention is also directed to a method for analyzing samples. In an embodiment, the method comprises disposing the base unit and the analysis unit in a connected configuration; transferring a reagent between the base unit reagent outlet and the analysis unit reagent inlet; disposing the base station and the analysis unit in a disconnected configuration; loading a sample into the analysis unit sample inlet; and processing the sample using the portable analysis device to obtain an analysis for the sample.

BRIEF DESCRIPTION OF THE DRAWINGS

The features, aspects and advantages of the present invention will become better understood with regard to the following description, appended claims and accompanying figures where:

DETAILED DESCRIPTION

Figure 1:
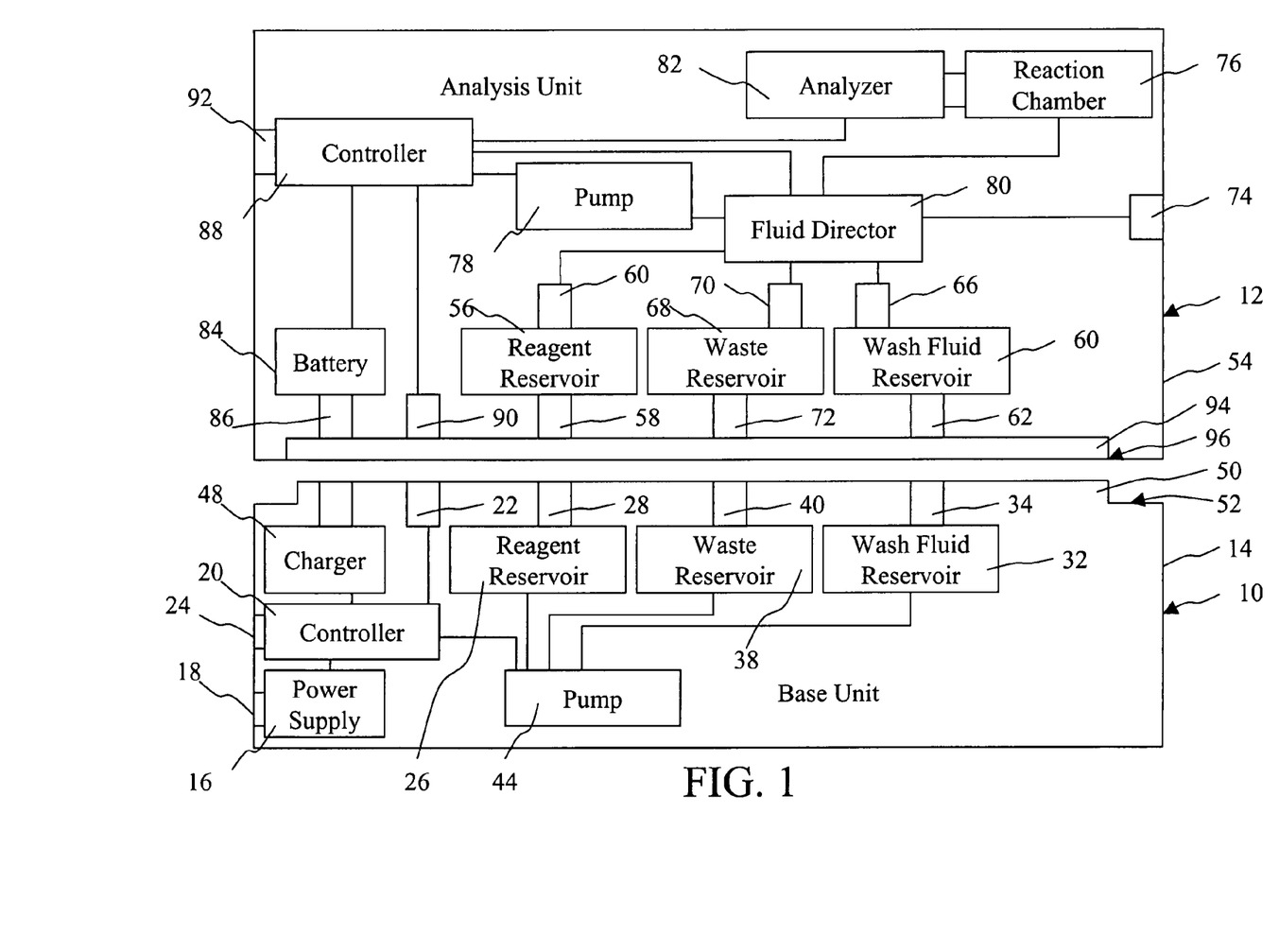
FIG. 1 is a schematic diagram of a portable analysis unit and a base unit according to one embodiment of the present invention.

The present invention has two major components. As shown in FIG. 1, the first component is a base unit 10, and the second is a portable analysis unit 12 designed to be coupled to the base unit 10. The analysis unit 12 is a standalone analysis device. The base unit 10 functions to support the analysis unit by supplying the portable analysis unit 12 with fluids and power.

In general, the analysis unit 12 is configured to receive and analyze a wide variety of samples and specimens. For example, samples may be biological specimens from a patient, but they may also be a wide variety of other biological, chemical, and environmental specimens having a component to be characterized or an analyte to be detected. One or more analytes may be detected at one time. In an embodiment of the present invention, the analysis unit produces measurements of those analytes comprising a "chem 8" panel (sodium, potassium, chloride, carbon dioxide, glucose, calcium, creatinine, and urea). Samples for the with the present invention may be obtained in the manner taught in co-pending U.S. patent application Ser. No. 10, 10/139,569, entitled WHOLE BLOOD SAMPLING DEVICE, filed on May 6, 2002, the entire contents of which are hereby incorporated herein by reference.

The analysis unit may be used to implement numerous specific analytical and/or preparative techniques, such as chromatography, PCR, LCR, enzymatic reactions, immunologic reactions, and the like. Samples will usually be liquid or be liquified prior to testing, and will frequently undergo a chemical or biochemical reaction prior to analysis. The analysis unit may provide for a variety of manipulations of the sample in addition to chemical and biological reactions, such as mixing, dispensing, valving, separation, heating, cooling, and the like.

The analytical systems may rely on numerous known detection techniques such as spectrophotometry, fluorometry, radiometry, magnatometry, galvanometry, reflectrometry, ultrasonic detection, mephlometry, electrophoretic measurement, temperature measurement, pressure measurement, potentiometric measurement, amperometric measurement, and the like. The analysis unit can employ aspects of "Multiplexed DNA Assays Using Structure-Specific Endonucleases", disclosed in U.S. patent application Ser. No. 10/420,322, filed on Apr. 22, 2003, and/or aspects of a "Method And Apparatus For Multiplex Flow Cytometry Analysis Of Diverse Mixed Analytes From Bodily Fluid Samples", disclosed in U.S. patent application Ser. No. 09/991,001, filed on Nov. 14, 2001, the entire contents of which are hereby incorporated by reference.

The Base Unit

Considering the base unit 10 in more detail, as shown in FIG. 1, the base unit 10 has an enclosure 14 which may be intended for mounting, e.g. on a floor, on a counter, in a rack, or in any other conventional manner, or which may be portable or hand-held. The base unit 10 includes a power supply 16 that may be coupled to an external power source (not shown), such as a 110 volt outlet, via a connector 18. The base unit also has a controller 20 with a microprocessor and a signal transmission circuit for controlling various functions of the base unit. Optionally, the controller 20 has a signal processor for analyzing and/or storing data received from the analysis unit through an information port 22. Optionally, a user interface 24 is coupled to the controller 20. The user interface 24 may include video monitors, alphanumeric displays, printers, LED displays, and the like. Additionally, the user interface 24 may include data entry devices, such as keyboards, touch screens, and the like. The user interface 24 may be provided on or in the enclosure, may be coupled to the base unit by a wire, or may communicate with the controller in the base unit via a wireless network.

The base unit has a reagent storage reservoir 26 for storing reagents for use in analyzing samples. A base unit reagent outlet 28 in fluid tight communication with the reagent storage reservoir 26 allows for reagent to be removed from the reagent storage reservoir. Preferably, the reagent outlet 28 also functions as an inlet for filling of the reagent reservoir 26. In a first additional embodiment, shown in FIG. 2, a base unit reagent inlet 30 allows for filling of the reagent storage reservoir 26. Multiple reagent storage reservoirs and outputs may be housed in the base unit depending on the analysis being conducted and the storage requirements of the reagents.

The base unit also has a wash fluid storage reservoir 32 for storing wash fluid for use in cleaning portions of the analysis unit 12. A wash fluid outlet 34 in fluid tight communication with the wash fluid storage reservoir 32 allows for wash fluid to be removed from the wash fluid storage reservoir 32. Preferably, the wash fluid outlet 34 also functions as an inlet for filling of the wash fluid storage reservoir. In a first additional embodiment, shown in FIG. 2, a base unit wash fluid inlet 36 allows for filling of the wash fluid storage reservoir.

The base unit has a waste fluid storage reservoir 38. A base unit waste fluid inlet 40 is in fluid tight communication with the base waste fluid storage reservoir 38. Preferably, the waste fluid inlet 40 serves as an outlet for draining of the waste fluid storage reservoir. In a first additional embodiment, shown in FIG. 2, a waste fluid outlet 42 is in fluid tight communication with the waste fluid storage reservoir 38 for removal of waste fluid from the waste fluid storage reservoir 38.

The base unit 10 has a pump 44 for providing fluids from each of the base unit storage reservoirs to its corresponding base unit outlet. Additionally, the base unit 10 has a charger 46 coupled to the power supply 16 for charging a battery in the analysis unit as discussed below. The base unit reagent outlet 24, wash fluid outlet 34, waste fluid inlet 40, and a charger connector 48 all protrude from the base unit and form a base unit interface 50.

The base unit includes an attachment region 52 for removably securing the analysis unit 12 to the base unit 10. The attachment region 52 may be any feature or structure on the enclosure 14 of the base unit 10 that can removably attach the analysis unit 12. The attachment region 52 is constructed so that the adapter can only be connected in a unique configuration so that the base interface is uniquely configured relative to the analysis unit. Often, the attachment region 52 defines a receptacle having dimensions which correspond to the outer peripheral dimensions of the analysis unit so that the analysis unit may be held in a desired orientation relative to the base unit. Alternatively, or in addition, pegs, pins, latches, or other attachment elements may be provided to hold the analysis unit on the base unit in a desired orientation.

The Analysis Unit

Considering the analysis unit 12 in more detail, as shown in FIG. 1, the analysis unit has an enclosure 54. Typically, the analysis unit 12 is substantially smaller than the base unit 10.

The analysis unit has a reagent supply reservoir 56 for storing reagents for use in analyzing samples. An analysis unit reagent inlet 58 in fluid tight communication with the reagent supply reservoir 56 allows for reagent to be loaded into the reagent supply reservoir. A reagent fluid outlet 60 in fluid tight communication with the reagent supply reservoir 56 allows fluid to be pumped from the reagent supply reservoir 56. Multiple reagent reservoirs and inputs may be housed in the analysis unit depending on the analysis being conducted and the storage requirements of the reagents.

The analysis unit also has a wash fluid supply reservoir 62 for storing wash fluid for use in cleaning portions of the analysis unit 12. A wash fluid inlet 64 in fluid tight communication with the wash fluid supply reservoir 62 allows for wash fluid to be loaded into the wash fluid supply reservoir 62. A wash fluid outlet 66 in fluid tight communication with the wash fluid supply reservoir 62 allows wash fluid to be pumped from the wash fluid supply reservoir 62. In an additional embodiment of the present invention, the analysis unit does not have the wash fluid supply reservoir 62, wash fluid inlet 64 and the wash fluid outlet 66 and excess reagent from the reagent reservoir 54 is used as a wash fluid.

The analysis unit has a waste collection reservoir 68. An analysis unit waste inlet 70 is in fluid tight communication with the waste collection reservoir 68. The waste inlet 70 allows waste, such as used wash fluid, reagents and sample to be pumped into the waste collection reservoir 68 for storage. A waste outlet 72 in fluid tight communication with the waste collection reservoir 68 serves as an outlet port for draining of the waste collection reservoir.

The analysis unit 12 also has a sample inlet 74. The sample inlet 74 allows for a sample to be loaded into the analysis unit. The analysis unit 12 has a reaction chamber 76 for conducting analysis of a sample. The analysis unit also has a pressure source such as a pump 78. The pump 78 is coupled to a fluid director 80 for directing fluid from one or more of the outlets of each of the analysis unit reservoirs, and the sample inlet 74, to the reaction chamber 76, and from the reaction chamber 76 to the waste fluid inlet 70. In an additional embodiment, the base unit 10 contains no pump and the analysis unit pump 78 transfers all fluids between the base unit and the analysis unit.

The analysis unit also has an analyzer 82, such as a chemical analyzer, for analyzing samples within the reaction chamber. The analysis unit has an electrical power component. In a preferred embodiment of the present invention, the electrical power component is a rechargeable battery 84 coupleable to a charger through a charging port 86. In an alternative embodiment of the present invention, the electrical power component is a regulator that may connected to an external power source, such as a 110 volt electrical outlet.

The analysis unit also has a controller 88 with a microprocessor and a signal transmission circuit for controlling various functions of the analysis unit. Optionally, the controller 88 has a signal processor for analyzing and/or storing data from experiments and from the base unit through information port 90. Additionally, the controller may have power conditioning, and monitoring components for optimally charging the rechargeable battery 84.

The controller 88 may contain a set of instructions for directing the automatic self-cleaning of the analysis unit. The controller may also contain a set of instructions for directing the automatic self-calibrating of the analysis unit. Additionally, the controller may contain a set of instructions for directing the automatic self-replenishing of reservoir fluids in the analysis unit. The controller may also contain a set of instructions for directing the automatic self-testing of the analysis unit.

Optionally, a user interface 92 is coupled to the controller. The user interface 92 may include video monitors, alphanumeric displays, printers, LED displays, and the like. Additionally, the user interface 92 may include data entry devices, such as keyboards, touch screens, and the like. The user interface 92 may be provided on or in the enclosure, may be coupled to the analysis unit by a wire, or may communicate with the controller in the analysis unit via a wireless network. In another embodiment, the controller is a personal digital assistant or other computer located outside of the analysis unit that is coupleable to the analysis unit to the control functions of the analysis unit.

In operation, each analysis uses the pump 78 and the fluid director 80 to apportion reagents, wash fluids, and sample from the reservoirs and the sample inlet to the reaction chamber and then to the analyzer according to the requirements of the analysis method. Expended fluids are collected in one or more waste reservoirs.

The analysis unit reagent inlet 58, wash fluid inlet 64, waste fluid outlet 72 and charging port 86 all protrude from the analysis unit and form an analysis unit interface 94. The analysis unit includes an attachment region 96 for removably securing the analysis unit 12 to the attachment region 52 of the base unit 10, as generally discussed above. The analysis unit interface 94 couples to the base unit interface 50 when the analysis unit attachment region 96 is mounted in the base unit attachment region 52. The connection of the interfaces provides power and/or fluids between the base unit and the analysis unit.

Electrical connections, both for power and signal transfer, will generally comprise conventional connectors in the form of electrodes, pins, plugs, zero insertion force (ZIF) connectors, and the like. Such electrical connections will usually require mating connectors in the interfaces which are brought together when the system is put together. The electrical connectors will often be present on a surface or edge of the analysis unit and base unit interfaces so that corresponding components will be engaged against each other when the analysis unit is mounted in the base unit.

Periodically, the analysis unit 12 is coupled to the base unit 10. When coupled, the base unit reagent outlet 28 is connected in fluid tight communication to the analysis unit reagent input 58, the base unit wash fluid outlet 34 is connected in fluid tight communication with the analysis unit wash fluid inlet 62, and the analysis unit waste fluid outlet 72 is in fluid tight communication with the base waste fluid inlet 40.

Coupling allows transfer of fluids between the supply reservoirs in the analysis unit and the storage reservoirs in the base unit. Expended fluids in the analysis unit 12 are replenished with fluids from the reservoirs in the base unit 10. Waste fluid is transferred from the analysis unit waste fluid reservoir 68 to the base unit waste fluid reservoir 40. Coupling also permits transfer of energy from the base unit charger 48 to the analysis unit battery 84.

Additionally, coupling allows transfer of information between the analysis unit controller 92 and the base unit controller 24. The units may cooperate to update information required for analysis, such as reagent lot-specific information, or sample test ordering information. Additionally, the units may cooperate to update software in the base unit 10 or the analysis unit 12. Additionally, the units may cooperate to download analysis results and performance data from the analysis unit. The analysis unit and the base unit may cooperate in testing and fault diagnosis, calibration of the analysis method, performance or quality control checks, and for more thorough cleaning of the analysis unit.

The storage reservoirs in the base unit are generally of greater capacity than the supply reservoirs in the analysis unit. The reservoirs in the base unit maybe stored under conditions more compatible with extended shelf life than are reasonable to incorporate within the relatively small volume of the analysis unit. A single base unit may support several analysis units. The reservoirs in the base unit may be replaced during periodic maintenance of the base unit.

Additional Components

The base unit and the analysis unit may have additional components depending on the type of analysis being conducted. In a first additional embodiment, shown in FIG. 2 the base unit has a support fluid storage reservoir 100, and a support fluid outlet 102 in fluid tight communication with the support fluid storage reservoir. Preferably the support fluid outlet 102 functions as a support fluid inlet. In an additional embodiment, a support fluid inlet 104 in fluid tight communication with the support fluid reservoir 100 allows for loading of the support fluid storage reservoir 100.

Figure 3:
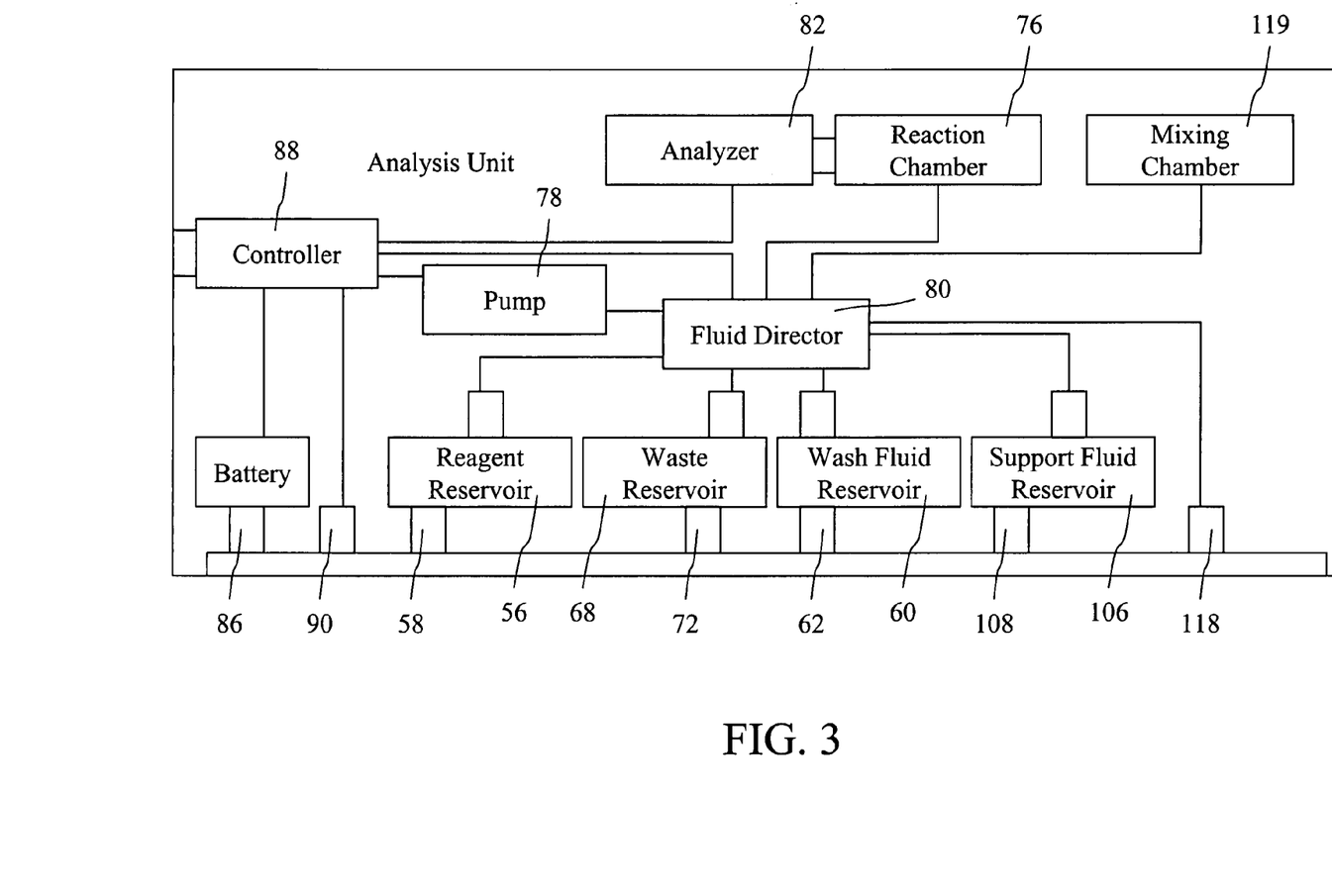
FIG. 3 is a schematic diagram of a portable analysis unit according to the first additional embodiment of the present invention

Additionally, as shown in FIG. 3, the analysis unit has a support fluid supply reservoir 106 and a support fluid inlet 108 in fluid tight communication with analysis unit support fluid supply reservoir 106 for filling of the support fluid supply reservoir 106. A support fluid outlet 110 in fluid tight communication with the support fluid supply reservoir 106 allows for fluid to be pumped from the support fluid supply reservoir.

Figure 2:
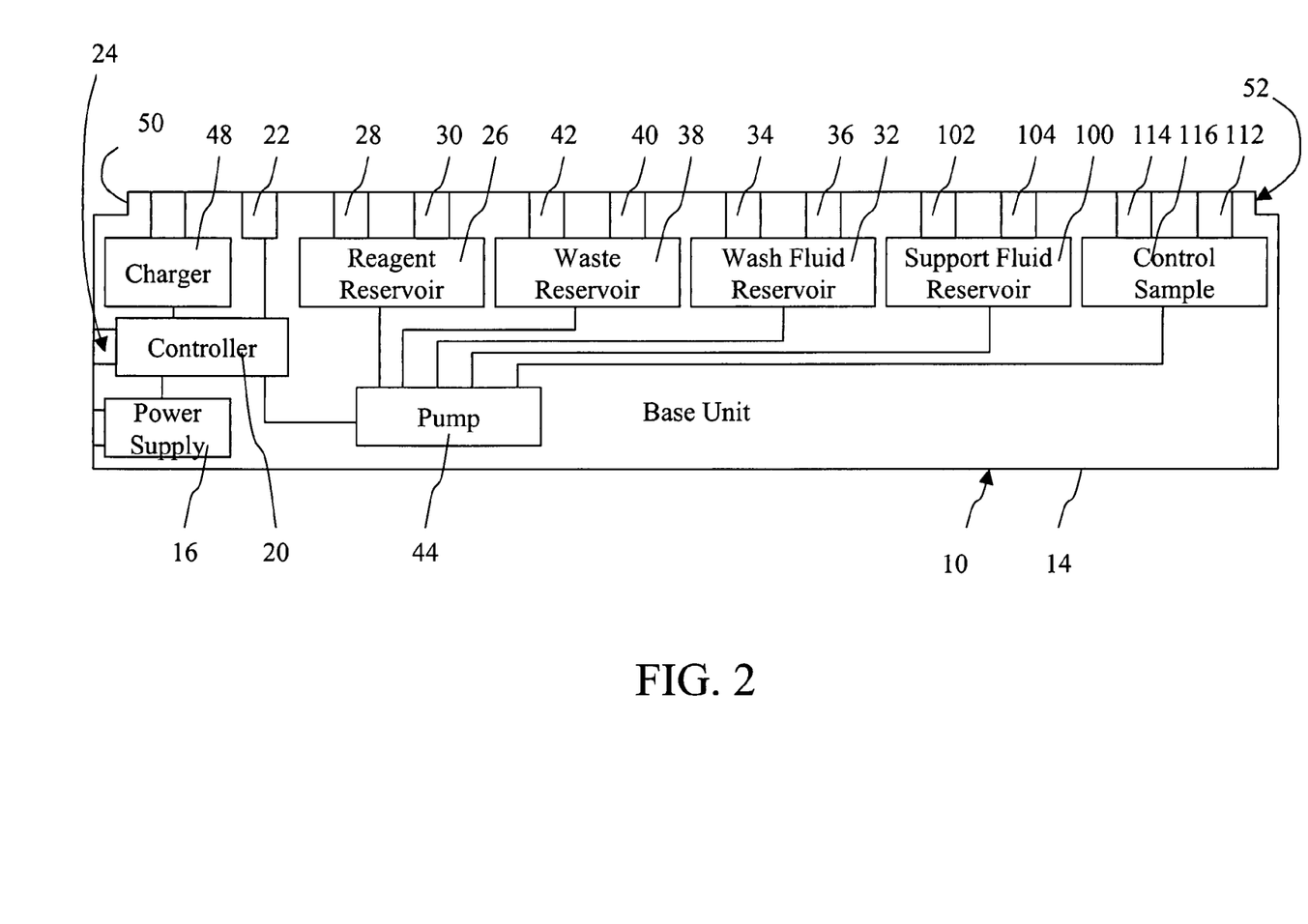
FIG. 2 is a schematic diagram of a base unit according to a first additional embodiment of the present invention.

Additionally, as shown in FIG. 2, the base unit has a control sample storage reservoir 112, and a control sample outlet 114 in fluid tight communication with the control sample storage reservoir 112. Preferably, the control sample outlet 114 functions as a control sample inlet.

In a first additional embodiment, as shown in FIG. 3, the analysis unit has a control sample inlet 118 for receiving control samples from the base unit. The samples received from the base unit may be analyzed for calibration or quality assurance purposes. Additionally, the analysis unit may have a mixing chamber 119.

When coupled together, the base unit support fluid outlet 102 is in fluid tight communication with the analysis unit fluid inlet 108, and the base unit control sample outlet 114 is in fluid tight communication with the analysis unit control sample inlet 118.

Construction of the Analysis Unit

The analysis unit has a manifold which is a channel network of vessels and passages wherein analytical steps are carried out and through which reactants are transported. Fluids from the various reservoirs and the sample inlet 74 are pumped by the pump 78 through the network of vessels and passages as directed by the fluid director 80.

In a preferred embodiment of the present invention, the manifold is produced by laminating essentially planar sheets of transparent material containing open troughs. Lamination of multiple planar sheets containing through holes produces a manifold with a three dimensional network of cavities.

Plastic sheets may be milled to produce troughs. The plastic sheets are then laminated by diffusion bonding. Alternatively, microfabrication techniques, such as casting from photochemically etched dies, may be used.

In a preferred embodiment, the manifold includes a cytometer flow cell 120 as part of the analyzer 82. The cytometer flow cell 120 includes a core stream hydrodynamically focused by a sheath flow. A flow cell may be formed in the manifold as illustrated in FIGS. 4 to 6.

Figure 4:
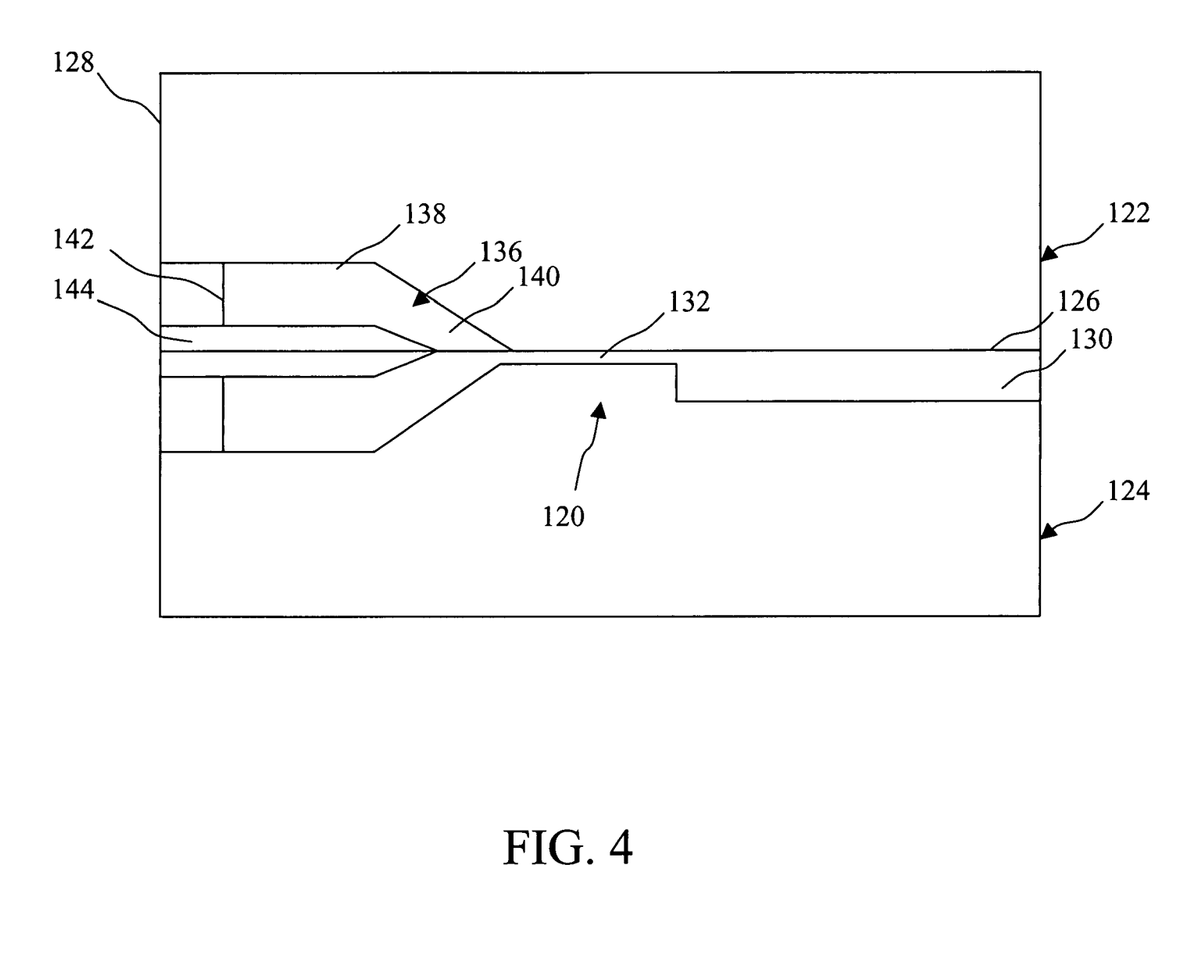
FIG. 4 is a side elevation view of a flow cytometer useful with the present invention.
Figure 5:
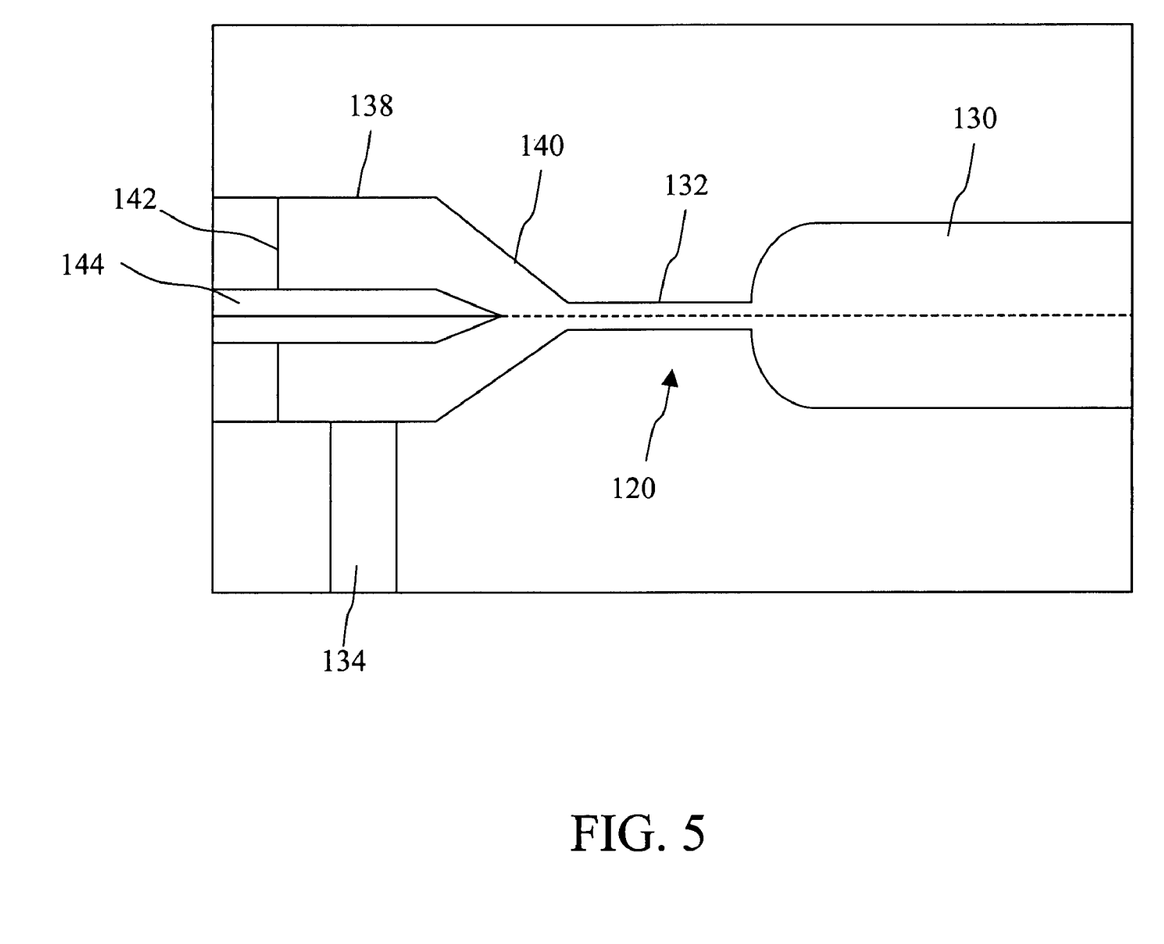
FIG. 5 is a top plan view of the flow cytometer in FIG. 4.
Figure 6:
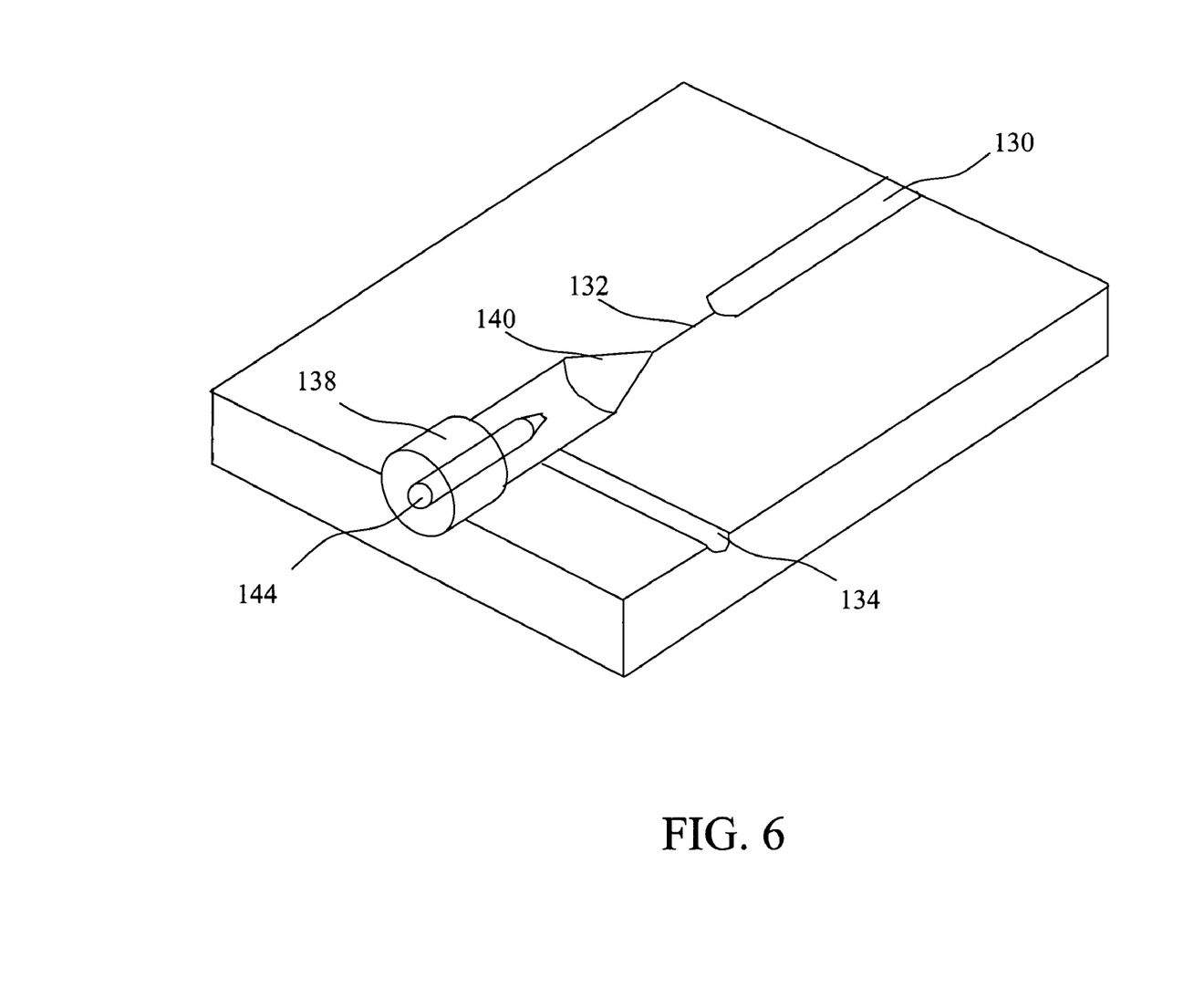
FIG. 6 is a perspective view of the flow cytometer of FIG. 4.

As shown in FIGS. 4 to 6, an upper transparent manifold sheet 122 and a lower transparent manifold sheet 124 meet at a lamination line 126 and have a common end surface 128. During fabrication, the lower manifold sheet 124 receives a drain channel 130 of relatively large dimension. In an embodiment, the drain channel 130 is preferably less than about 2 mm by about 2 mm in cross-section. The drain channel 130 may be produced by conventional milling.

Preferably, the lower manifold sheet 124 also receives an optical channel 132 of from about 50 µm by 50 µm in cross section to about 1000 µm by 1000 µm in cross section. The optical channel may be produced by thermal embossing with a polished master. Alternatively, the optical channel may be produced by slit sawing followed by polishing for a good optical surface. The projections of a long axis of the drain channel and the optical channel onto the surface are collinear. Preferably, the channels intersect at a point which is several millimeters away from the end surface 128. Preferably, the optical channel 132 extends approximately 1 mm to 10 mm, and more preferably about 5 mm from the point of intersection toward the end surface.

A sheath feed channel 134 extends from at least one side toward the collinear axis of the drain channel 130 and the optical channel 132. Once the manifold sheets are laminated, the end surface 128 is faced off to assure alignment. A bore 136 is drilled from the end surface 128 along the collinear axis of the drain channel 130 and the optical channel 132 in alignment with a center of the cross-section of the optical channel 132. The bore 136 intersects the now covered optical channel 132 creating a continuous passageway beginning at the end surface comprising sequentially: the bore 136, the optical channel 132, and the drain channel 130. The bore 136 also intersects the sheath feed channel 134 allowing fluid tight communication therewith.

The bore 136 has a straight section 138 of constant diameter and a tapered section 140 of diminishing diameter. The tapered section 140 is in fluid tight communication with the optical channel 132 and acts as a necking down region of the flow cell 120. A compliant collar 142 is sized to form a fluid tight seal in the straight section of the bore. The collar 142 has a through hole concentric with the collar diameter. The through hole is sized to form a fluid tight seal with an injector tip 144. The injector tip is preferably a tapered ceramic wire bonding capillary such as those manufactured by Kulicke & Soffa Industries, Inc. The collar 142, tip 144 and bore 136 are aligned so that the tapered end of the tip is centered within the straight section of the bore. The collar 142 and the bore 136 may have additional geometry to assure precise alignment.

In operation, sheath fluid flows through the sheath feed channel 138 and suspended particles to be analyzed flow through the injector tip 144. Viscous interactions between the flowing sheath fluid and the core stream injected by the injector tip 144 produce a uniform velocity profile for the core stream and the immediately surrounding portion of the sheath fluid. A low Reynolds number of the flow stream and a smooth profile of the cell prevent turbulence. The core stream delivered by the flow injector tip 144 is hydrodynamically focused to a smaller diameter by the tapered section of the bore. This reduces the core stream diameter within the optical channel to close to that of the particle diameter without requiring a small and easily clogged injector tip.

Positive pressures drive the fluids through the flow cell 120 to avoid the formation of micro-bubbles that may interfere with measurement. Core and sheath flows in most cytometer cells use differential drive pressures to optimize the flow rates through channels with different flow resistance. An alternative that reduces the amount of active components is to use a single pressure source and tune the flow resistances to achieve the desired relative flows.

In a preferred embodiment of the present invention, the reservoirs are formed as long, thin tubes. Surface tension between the tube wall and the reactant prevents bubbles of air from bypassing liquid in the tube. The contact angle between the tube material and the reactant determines the tube diameters that will prevent bypass. Tube diameter may range from fractions of a millimeter to several millimeters depending on the tube material and on surfactants in the fluid.

A tube reservoir may be vented at one end without significant evaporation. The tube format of the reservoirs is advantageous in that flushing from a distal end easily purges the reservoir. This is especially advantageous for reagents with a limited shelf life because expired materials may be thoroughly removed before refilling. A small diameter tubular reservoir has the disadvantage that it exposes a large surface area to the reactant. The large surface area exposure may not be important for wash buffers, but can lead to changes in a reactant upon storage. Gas exchange and water loss through permeable tube materials are also important considerations in selecting the appropriate reservoir material. Appropriate reservoir materials include, for example, polyethylene, polypropylene, PTFE and PEEK.

In an alternative embodiment, the reservoirs are formed as collapsible containers. A collapsible container may be more difficult than a thin tube to flush, but is likely to be appropriate for relatively large volumes of simple reagents such as sheath fluid and rinse fluid. Since these simple fluids form a significant quantity of all liquids in the system, the simple fluids may be placed in a collapsible waste reservoir configured as a dual bag with a common wall. Collapsible containers do not need venting for fluid transfer.

The analyzer of the present invention needs a clean liquid sample. A clean liquid sample may be provided by traditional methods, such as centrifugation or evacuated draw tubes with capillary transfer, or by a specialized sampling device. Regardless of the method of sampling, the aspirated specimen is likely to be preceded by a variable amount of air. The pump 78 may be used to dispense the first portion of the sample aspirate to the waste reservoir 68 to dispose of the air. The volume dispensed to the waste reservoir 68 may be determined either empirically or by monitoring a bubble sensor on the channel from the sample inlet 74.

Considering the analysis unit pump 78 in more detail, the pump is preferably a positive displacement pump with controllable dispense volumes. A pump without precisely controllable dispense volumes may overfill vessels or channels in the manifold. The volume transferred is then defined by the volume of geometrical features in the manifold. This may be adequate for a multiplexing system as its operation can be stereotypical with the pump using the same operation sequence for each analysis. A single pump is preferred over multiple pumps, because although this slows down operation by converting parallel actions to serial actions, a single pump reduces device complexity and size.

Considering the fluid director 80 in more detail, the fluid director couples the pump 78 to different flow channels at different stages of the analysis. The fluid director 80 may be a multiport valve or an array of separate valves. Each functional element within the manifold, such as the reaction chamber 76, the sample inlet 74, the reagent supply reservoir 56, and if present, the flow cell core stream, connects to a valve port. Each valve port may be selectively connected by valve action to the pump.

Operations proceed sequentially, with the pump 78 connected to a first functional element for a first operation and then to a second functional element for a second operation and so forth. For example, with the fluid director 80 coupling the pump 78 to the reagent supply reservoir 56, the pump aspirates a measured amount of reagent. The fluid director 80 then couples the pump 78 to the reaction chamber 76 where the pump dispenses the measured reagent volume. Later operations serve to transfer sample from the sample inlet to the reaction vessel, to transfer the reaction mixture from the reaction vessel to the flow cell core stream, and to operate the flow cell for measurement.

Some functional elements require only a single connection via the fluid director 80. Examples of functional elements requiring only a single connection include vented or collapsible reservoirs, the sample inlet 74 which is vented through the sampling device, and the flow cell which is plumbed to the waste reservoir. The reaction chamber 76 requires two connections for rinsing.

Figure 7:
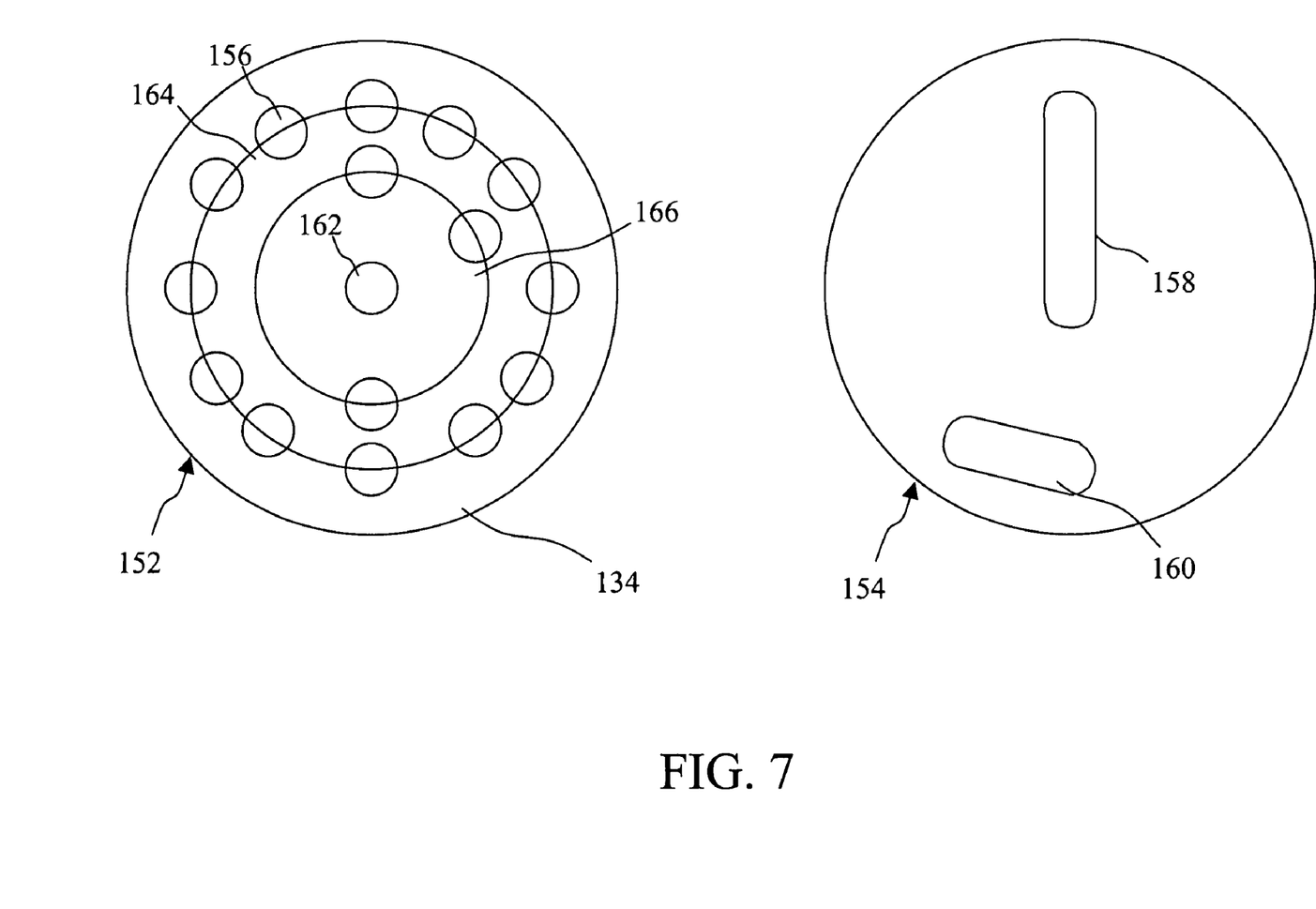
FIG. 7 is a schematic diagram of a fluid director useful with the present invention.

FIG. 7 shows a multiport valve fluid director 14 according to a preferred embodiment of the present invention. The multiport valve shown in FIG. 7 is a rotary shear valve. The valve has two disks, a stator disk 152 and a rotor disk 154, each disk having flat ground surfaces in contact. The stator disk 152 is fixed to a valve interface manifold (not shown). The rotor disk 154 is aligned to the stator disk 152 and may be rotated with respect to the stator by a motor or other actuator. The stator disk 152 is pierced by a collection of holes 156 that form fluid conduits. The rotor 154 has a radial incised channel 158 and a tangential incised channel 160 that form fluid tight channels when the stator 152 is brought into contact with the rotor 154. There are no holes in the rotor 154.

The stator 152 has a central hole 162, holes on a first radius 164, and holes on a second smaller radius 166. The radial channel 158 on the rotor 154 connects the central hole 162 to holes on both radii 164, 166. The tangential channel 160 connects two adjacent holes on the first radius 164. There is one relative orientation of the stator 152 and the rotor 154 when the radial channel 166 connects the central hole 160 to holes on both the first radius 162 and the second radius 164. This orientation permits the pump, connected to the central hole, to propel fluid through two passages simultaneously. This orientation may be used to drive core and sheath fluid in the flow cell.

Driving rotation of the fluid director 80 is an actuator (not shown) that may extend a distance from the rotor 154 and the stator 152. The actuator is preferably a miniature stepping motor with a gearhead and an indexer such as a MicroMo AM1020 with a 10/1 gearhead. The fluid director 80 may be mounted along the edge of the analysis not manifold to conserve space. A coupling manifold (not shown) connects holes on the two radii 162, 164 of the stator 152 to channels formed in the manifold of the analysis unit. The coupling manifold may be laminated to the manifold, or it may be removably mounted with the aid of gaskets, other seals, or ground flat surfaces on contact. Removable mounting is advantageous when the manifold contains added components on the mounting surface, such as the inserted collar and injection tip of the flow cell.

Rotating the rotor 154 with respect to the stator 152 selectively couples channels within the manifold to the pump 78. The radial channel 158 of the rotor 154 aligns with a hole on the stator 152 plumbed to the desired channel. The pump 78 then aspirates or dispenses the required quantity of fluid through its connection at the central hole 162. The actuator repositions the fluid director 80 to transfer the fluid to another channel of the manifold. This permits an arbitrary sequence of fluidic operations.

The tangential channel 160 in the rotor connects a second channel in the manifold to a third channel in the manifold while the pump connects to the first channel. Such a connection is useful for venting a channel during fluid transfer or for flushing the contents of a channel to waste for cleaning. The distribution of holes on the larger radius 164 of the stator activates this feature only for appropriate channels.

Considering the reservoirs in more detail, fluid in the reservoirs may develop a hydrostatic pressure at the outlet due to variations in fill volume, position, temperature, or compliance of the container. The hydrostatic pressure may cause unintended flow during valve state transition. Placement of conduits connected to reservoirs on the smaller radius circle, prevents their coupling to other conduits by the tangential channel as it sweeps by.

A table summarizing an example set of connections from stator holes 56 to channels in the manifold and the functions enabled by aligning the radial channel of the rotor with each "clock" position is shown in Table I below. The exemplary table assumes a single reagent, no separation steps, a flow cytometer as the analyzer, and a common sheath/wash fluid. Those skilled in the art will recognize that the series of steps will be altered depending on the number of reagents, the nature of the reaction, and the analyzer.

In Table I, two waste ports are plumbed to a single waste reservoir. The reaction chamber is filled from a proximal side and drained through a distal side. The core channel of the flow cell is filled via a core fill loop prior to operating the flow cell.

TABLE I

| Radial Conduit "clock" Position | Smaller Radius Connection | Larger Radius Connection | Tangent Channel Connection | Function |
| --- | --- | --- | --- | --- |
| 1 | None | Sample Flush channel | Sample-waste | Rinse sample path |
| 2 | Reagent Reservoir | None | Proximal reaction chamber-waste 1 | Aspirate reagent |
| 3 | None | Reaction chamber, distal side | Proximal reaction chamber-waste 2 | Rinse reaction chamber |
| 4 | None | Air/vent | Proximal core fill loop-waste 2 | Aspirate air |
| 5 | None | core fill loop, distal side | Proximal core fill loop-core | Fill core of flow cell |
| 6 | Wash/sheath fluid reservoir | None | Core-sample flush | Aspirate wash/sheath fluid |
| 7 | None | Sample inlet | None | Aspirate sample |
| 8 | None | Waste 1 reservoir | None | Dispense to waste |
| 9 | None | Reaction chamber, proximal side | Distal reaction chamber-vent | Fill reaction chamber |
| 10 | None | Waste reservoir | Distal core fill loop - vent | None |
| 11 | None | Core fill loop, proximal side | None | None |
| 12 | Sheath | Core | None | Operate flow cell |

Table II below shows an operation sequence useful for the above embodiment. A sample is placed in the sample inlet 74 and the steps listed in Table II are performed. The fluid director position is indicated by the clock position of the radial channel in the rotor. Following performance of the steps listed in Table II analysis of the sample is completed and the analysis unit ready for reuse.

TABLE II

| Step | Fluid Director (Rotor) Position | Action |
| --- | --- | --- |
| 1 | 2 | Aspirate reagent |
| 2 | 9 | Dispense reagent to reaction chamber |
| 3 | 8 | Flush pump line to waste |
| 4 | 6 | Aspirate wash fluid to refill pump |
| 5 | 7 | Aspirate sample air |
| 6 | 8 | Dispense sample air to waste |
| 7 | 7 | Aspirate sample |
| 8 | 9 | Dispense sample: chase sample with wash |
| 9 | 8 | Flush pump line to waste |
| 10 | 6 | Aspirate wash fluid to refill |
| 11 | 12 | Dispense wash fluid to sheath and core |
| 12 | 6 | Aspirate wash fluid to refill |
| 13 | 9 | Aspirate reaction aliquot |
| 14 | 5 | Dispense to core via core fill loop: chase with wash |
| 15 | 8 | Flush pump line to waste |
| 16 | 6 | Aspirate wash fluid to refill pump |
| 17 | 12 | Dispense to operate flow cell |
| 18 | 6 | Aspirate wash fluid to refill pump |
| 19 | 1 | Dispense to sample flush channel to clean sample channel |
| 20 | 6 | Aspirate wash fluid to refill |
| 21 | 3 | Dispense to flush reaction chamber to waste |
| 22 | 9 | Aspirate to drain reaction chamber |
| 23 | 8 | Dispense to waste, flush pump line |
| 24 | 6 | Aspirate fluid to refill pump |

The exemplary sequence detailed above requires 24 to 30 valve and pump actions (depending on the number of repeat cycles for thorough washing). The exemplary sequence is a simplified sequence appropriate for single reagent analysis without separation steps. Such a sequence is likely to be useful for high concentration analytes such as electrolytes and metabolites. Addition of a second reagent (containing reporter molecules, etc.) and separator functions, require additional valve ports and manifold channels. Cellular analysis requires a second sample path and a different sampling device.

An analyzer according to a preferred embodiment of the present invention includes one or more excitation sources. In a preferred embodiment, at least one of those excitation sources is a diode laser operating in the red and near infrared region with associated drive, control and monitoring circuitry. The analyzer also includes optical components to shape and direct excitation beams and admitted light. The analyzer also includes filters and dichroics to select excitation and emission wavelengths. Finally, the analyzer includes detectors to convert light into electrical signals.

The present invention allows for the distribution of functions between multiple units to maximize portability while continuing to support advanced capabilities that otherwise would have to be performed manually. Additionally, the present invention allows for the reuse of wetted parts. Although a disposable unit may be appropriate for sample collection or separation, the present clinical analysis system follows the model of central laboratory instruments, wherein the analysis apparatus is cleaned and reused automatically after each use.

These features reduce the costs of operation compared to prior art methods of analysis. Costs are reduced by the elimination of sample transfer costs associated with a central laboratory. Costs are also reduced by the reduction of labor and direct costs associated with calibration and quality control, and by the reduction in downtime due to asynchronous maintenance of the base station and analysis unit.

The present invention eliminates costs associated with transport of samples to the central laboratory. These costs are not simply courier costs. Because central laboratories have multiple samples, each sample container must be uniquely identified. Individual sample containers do not have to be uniquely identified if only one sample is processed at a time. Sample identification information may be directly entered from patient identification. The present invention also reduces the likelihood of mixing up samples, a very large source of laboratory errors.

The present invention is differentiated from other point of need devices by further savings. The reuse of the analysis units eliminates costs associated with single-use units. Packaging costs for disposable units often exceeds the normal reimbursement level for a clinical chemistry test. Disposable units also introduce indirect cots. Disposable units must be individually removed and replaced. Moreover, the disposable unit may contain potentially infectious material after use so that they may not be casually discarded. The handling steps necessary with disposable units increase the burden on the test operator.

The features of the present invention further reduce costs by automating certain tasks that are normally done manually even in the central laboratory. The base station performs routine maintenance, calibration, and quality control. These tasks are particularly onerous in a point of need environment, especially where the operators are not specialists in analysis and may be unfamiliar with the requirements and procedures. The invention may also reduce the amount of labor required by the operator as compared to drawing blood, labeling a sample, and transporting the sample required when using the central laboratory.

Additionally, the system of the present invention may reduce costs associated with system downtime, because of the asynchronous nature of maintenance between the analysis units and the base unit. The analysis unit is maintained when convenient for the operator by coupling the analysis unit to the base unit. The base unit is maintained, probably by central laboratory personnel, on a relatively fixed schedule to replace reservoirs. Maintenance of the base unit does not prevent further analysis by the analytical unit. Maintenance of a single analytical unit does not prevent further analysis by other analytical units, in contrast to traditional analytical units, where functions are not divided, and if the system is unavailable, the operator must wait.

In an alternative version of the present invention, the functions of the portable component and the base unit are reversed. In some settings, such as a doctor's office, a bench top base unit that conducts analysis is acceptable. But the typical absence of analytical expertise among office staff still make the automated replenishment, calibration, and quality control features of the present invention desirable. These functions could be incorporated in a portable unit that is transported periodically from site to site.

Although the present invention has been described in considerable detail with reference to certain preferred versions thereof, other versions are possible. Therefore, the spirit and scope of the appended claims should not be limited to the description of the preferred versions described herein.

All features disclosed in the specification, including the claims, abstracts and drawings, and all the steps in any method or process disclosed, may be combined in any combination except combination where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. §112.

What is claimed is:

1. A system for analyzing samples comprising:
 a) a portable analysis unit comprising:
  i) a sample inlet;
  ii) an analyzer for determining a characteristic of a sample and providing data about the characteristic;
  iii) a reagent supply reservoir;
  iv) a collection reservoir for waste comprising used reagent and analyzed sample;
  v) a reagent inlet for providing reagent to the supply reservoir;
  vi) a waste outlet for removing waste from the collection reservoir;
  vii) a supply conduit from the reagent supply reservoir to the analyzer;
  viii) a waste conduit from the analyzer to the collection reservoir;
  ix) an analysis unit power source for providing power to the analyzer;
  x) a data output element for outputting data generated by the analyzer;
  xi) a pressure source for moving reagent and waste; and
 b) a base unit adapted for connection to the analyzer unit for providing reagent to the analysis unit and receiving waste from the collection reservoir, the base unit comprising:
  i) a reagent storage reservoir;
  ii) a waste storage reservoir;
  iii) a waste inlet for connection to the waste outlet of the analysis unit for receiving waste from the analysis unit; and
  iv) a reagent outlet for providing reagent from the reagent storage reservoir to the reagent inlet of the analysis unit;
 wherein the base unit and the analysis unit are adapted to be disposed in: a disconnected configuration wherein the analysis unit is separate from the base unit or
 a connected configuration wherein the reagent outlet is connected to the reagent inlet and the waste inlet is connected to the waste outlet; and
 wherein the analysis unit is capable of analyzing a sample while in the disconnected configuration, and
 wherein the analysis unit power source comprises a rechargeable battery; and
 the base unit further comprises a battery charger connectable to the analysis unit power source.

2. The system for analyzing samples of claim 1 wherein the portable analysis unit further comprises a multiport valve coupled to the pressure source, the supply conduit and the waste conduit.

3. The system for analyzing samples of claim 2 wherein the portable analysis unit further comprises a reaction chamber coupled to the multiport valve.

4. The system for analyzing samples of claim 2 wherein:
 the analysis unit further comprises:
  a wash fluid supply reservoir coupled to the multiport valve; and
  a wash fluid inlet for providing wash fluid to the wash fluid supply reservoir; and
 the base unit further comprises:
  a wash fluid storage reservoir; and
  a wash fluid outlet for providing wash fluid from the wash fluid storage reservoir to the wash fluid inlet of the analysis unit.

5. The system for analyzing samples of claim 2 wherein:
 the analysis unit further comprises:
  a support fluid supply reservoir coupled to the multiport valve; and
  a support fluid inlet for providing support fluid to the support fluid supply reservoir; and
 the base unit further comprises:
  a support fluid storage reservoir; and
  a support fluid outlet for providing support fluid from the support fluid storage reservoir to the support fluid inlet of the analysis unit.

6. The system for analyzing samples of claim 2 wherein the portable analysis unit further comprises a controller controlling the analyzer and the multiport valve.

7. The system for analyzing samples of claim 6 wherein the controller comprises a microcomputer capable of inputting data and outputting data.

8. The system for analyzing samples of claim 7 wherein the analysis unit further comprises a user input device for inputting data into the analysis unit microcomputer.

9. The system for analyzing samples of claim 6 wherein the controller contains a set of instructions for directing the automatic self-cleaning of the analysis unit.

10. The system for analyzing samples of claim 6 wherein the controller contains a set of instructions for directing the automatic self-calibrating of the analysis unit.

11. The system for analyzing samples of claim 6 wherein the controller contains a set of instructions for directing the automatic self-replenishing of reagents in the reagent supply reservoir.

12. The system for analyzing samples of claim 6 wherein the controller contains a set of instructions for directing the automatic self-testing of the analysis unit.

13. The system for analyzing samples of claim 1 wherein the base unit further comprises a pump for providing reagents from the reagent storage reservoir to the portable analysis unit reagent inlet.

14. The system for analyzing samples of claim 13 wherein the base unit further comprises a controller coupled to the base unit pump.

15. The system for analyzing samples of claim 14 wherein the base unit further comprises a user input device for inputting data into the base unit controller.

16. The system for analyzing samples of claim 1 wherein:
the portable analysis unit further comprises:
a control sample inlet; and
the base unit further comprises:
a control sample storage reservoir; and
a control sample outlet for providing control sample from the control sample storage reservoir to the control sample inlet.

17. The system for analyzing samples of claim 1 wherein the analyzer is a cytometer flow cell.

18. The system for analyzing samples of claim 17 wherein the cytometer flow cell comprises a core stream hydrodynamically focused by a sheath flow.

19. The system for analyzing samples of claim 1 wherein the pressure source is a pump.

20. A method for analyzing samples comprising:
a) selecting the portable analysis unit of claim 1;
b) obtaining a sample;
c) entering the sample into the sample inlet; and
d) analyzing the sample using the portable analysis unit of claim 1 to obtain an analysis for the sample.

21. A method for analyzing samples using the system for analyzing samples of claim 1, the method comprising:
a) disposing the base unit and the analysis unit in the connected configuration;
b) transferring a reagent between the base unit reagent outlet and the analysis unit reagent inlet;
c) disposing the base station and the analysis unit in the disconnected configuration;
d) loading a sample into the analysis unit sample inlet; and
e) processing the sample using the portable analysis device to obtain an analysis for the sample.

22. A modular analyzing device comprising:
a) an analysis unit comprising:
i) a reagent supply reservoir;
ii) a reagent inlet for providing reagent to the reagent supply reservoir;
iii) a wash fluid supply reservoir;
iv) a wash fluid inlet for providing wash fluid to the wash fluid supply reservoir;
v) a support fluid supply reservoir;
vi) a support fluid inlet for providing support fluid to the support fluid supply reservoir;
vii) a waste collection reservoir;
viii) a waste outlet for removing waste from the waste collection reservoir;
ix) a sample inlet;
x) a pressure source;
xi) a reaction chamber;
xii) a multiport valve disposed in fluid tight communication with the sample inlet, the supply reservoirs, the pressure source, the reaction chamber and the waste collection reservoir;
xiii) an analyzer for determining a characteristic of a sample and providing data about the characteristic, the analyzer being coupled to the reaction chamber; and
xiv) an analysis unit power source;
b) a base unit comprising:
i) a base unit reagent storage reservoir;
ii) a base unit reagent outlet for providing reagent from the reagent storage reservoir to the reagent inlet of the analysis unit;
iii) a base unit wash fluid storage reservoir;
iv) a base unit wash fluid outlet for providing reagent from the wash fluid storage reservoir to the wash fluid inlet of the analysis unit;
v) a base unit control sample storage reservoir;
vi) a base unit control sample outlet for providing control sample from the control sample storage reservoir to the control sample inlet of the analysis unit;
vii) a support fluid storage reservoir;
viii) a support fluid outlet for providing support fluid from the support fluid storage reservoir to the support fluid inlet of the analysis unit;
ix) a waste storage reservoir; and
x) a waste inlet for connection to the waste outlet of the analysis unit for receiving waste from the analysis unit; and
c) a controller comprising: a microcomputer capable of outputting data and a user input device for inputting data into the microcomputer;
wherein the controller has a set of instructions for at least one of: directing the automatic self-cleaning of the analysis unit, directing the automatic self-calibrating of the analysis unit, directing the automatic replenishing of reservoir fluids in the analysis unit, and directing the automatic self-testing of the analysis unit; and
wherein the base unit and the analysis unit are adapted to be disposed in:
a disconnected configuration wherein the analysis unit is separate from the base unit or
a connected configuration wherein the reagent outlet is connected to the reagent inlet, the wash fluid outlet is connected to the wash fluid inlet, the support fluid outlet is connected to the support fluid inlet, and the control sample outlet is connected to the control sample inlet,
wherein the analysis unit power source comprises a rechargeable battery; and
the base unit further comprises a battery charger connectable to the analysis unit power source.

* * * * *